United States Patent [19]

Ecke, Jr.

[11] Plant 4,950

[45] Nov. 16, 1982

[54] POINSETTIA NAMED PINK CURLY

[75] Inventor: Paul Ecke, Jr., Encinitas, Calif.

[73] Assignee: Paul Ecke Ranch, Encinitas, Calif.

[21] Appl. No.: 255,819

[22] Filed: Apr. 20, 1981

[51] Int. Cl.[3] ..... A01H 5/00

[52] U.S. Cl. ..... Plt./86

[58] Field of Search ..... Plt./86

*Primary Examiner*—Robert E. Bagwill

*Attorney, Agent, or Firm*—Chas W. Rummler

[57] ABSTRACT

A new pink poinsettia of the "curly" type which originated as a hybrid seedling and is distinguished by the extraordinary shape of its leaves and bracts which grow abundantly on strong, straight stems of medium height. The wide bracts overlap each other in a more-or-less counterclockwise fashion and form a round cushion-like appearance atop a column of many green leaves carried on a relatively heavy stem.

2 Drawing Figures

BACKGROUND OF THE NEW PLANT

This poinsettia variety was produced as a hybrid by crossings of various seedlings or mutations, including Ecke's Flaming Sphere (U.S. Plant Pat. No. 1,052), done at my breeding facilities at Encinitas, Calif., and this plant was selected by me from among many pink curly seedlings as the best of the pink colors. I reproduced this new plant in greenhouse at Encinitas by means of cuttings and several generations of such propagation of this variety have demonstrated that its novel characteristics hold true from generation to generation and appear to be firmly fixed.

DESCRIPTION OF THE DRAWINGS

This new poinsettia cultivar is illustrated by the accompanying full color photographic drawings, in which the upper one shows a side view of a potted plant and the lower one shows a full face view of the inflorescence and the surrounding cushion of bracts, the colors shown being as nearly true as it is reasonably possible to obtain by professional photographic procedures.

DESCRIPTION OF THE NEW PLANT

The following is a detailed description of this new variety of poinsettia plant as observed in greenhouse at Encinitas, Calif., with the color designations being stated according to The R.H.S. Colour Chart published by The Royal Horticultural Society of London, England.

THE PLANT

Origin: Seedling.

Parentage: Direct parentage is unknown but the line includes Ecke's Flaming Sphere (U.S. Plant Pat. No. 1,052).

Classification:

*Botanic.*—*Euphorbia pulcherrima.*

*Commercial.*—Pot poinsettia.

Form: Shrub, with upright and moderately stiff stems.

Height: Medium. Comparable to most modern commercial poinsettia varieties.

Growth habit: Vigorous with little tendency to branch. When a stem is pinched back, only two or three branches will form. Cuttings from this plant produce roots under greenhouse conditions in a manner similar to that of other poinsettia varieties.

Growth rate: Normal for poinsettias.

Foliage: Abundant with good retention.

*Leaf shape.*—The leaf shape is predominantly ovate and often dentated. Most leaves are mono or bi-lobed on each side of the midrib and the midrib is convoluted or curled, often through as much as 200° of arc with the upper surface of the leaf being the outer surface of the curve. The unique appearance of the leaves and bracts may be described as though puckered and arched as by a foreshortening of the leaf midrib as might be caused by pulling a drawstring inside the midrib.

*Leaf size.*—The leaves average about 2 to 5 inches long as measured along the curved midrib and about 2½ to 4 inches wide.

*Aspect.*—Upper side — dull with veins indented. Under side — dull with ordinary veining.

*Color.*—Upper side — very close to RHS 137A. Under side — near and between RHS 146A and 147B.

Bracts: The bracts are abundant with an overlapping arrangement and with a very tight center, thus forming a round cushion-like appearance with an average diameter of from 5 to 7 inches and with the individual bract tips forming a counterclockwise swirl when looking down into the top of the plant.

*Size.*—Bracts are usually in the range of 2½ to 4 inches long.

*Shape.*—Generally ovate with long acuminate tip. The appearance is somewhat puckered and there is a strong tendency for the ends to curl.

*Petioles.*—The petioles are quite short and are inconspicuous.

*Color.*—Upper side — near and between RHS 51A and 52A. Under side — near 51B.

*Ribs and veins.*—The ribs and veins are near the color of the bracts and are therefore inconspicuous.

*Retention.*—Good. The bracts last longer than the leaves.

I claim:

1. A new and distinct poinsettia cultivar, substantially as herein shown and described, distinguished by its many bracts of a solid pink overall color which appear in overlapping arrangement and tightly centered about the central cluster of flowers, the long tips of the bracts tending to form a counterclockwise swirl.

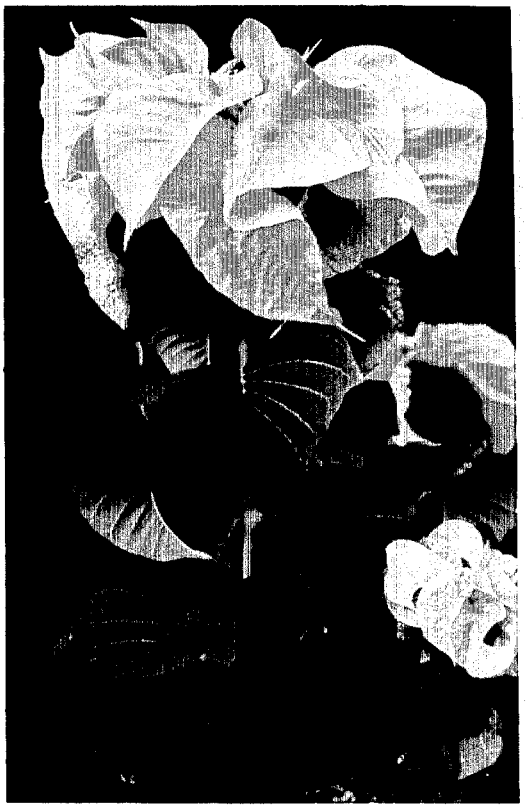
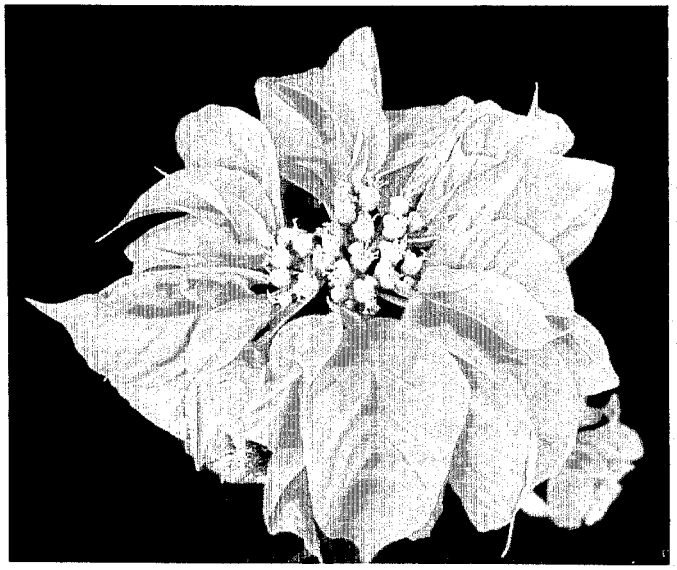

* * * * *